(12) United States Patent
Kritzler et al.

(10) Patent No.: US 8,795,740 B2
(45) Date of Patent: Aug. 5, 2014

(54) DRIP TRAY TABLET

(75) Inventors: Steven Kritzler, Cronulla (AU); Alex Sava, Paddington (AU)

(73) Assignee: Novapharm Research (Australia) Pty Ltd, Rosebery, New South Wales (AU)

( * ) Notice: Subject to any disclaimer, the term of this patent is extended or adjusted under 35 U.S.C. 154(b) by 2172 days.

(21) Appl. No.: 10/576,862

(22) PCT Filed: Oct. 20, 2004

(86) PCT No.: PCT/AU2004/001438
§ 371 (c)(1),
(2), (4) Date: Jan. 3, 2007

(87) PCT Pub. No.: WO2005/041659
PCT Pub. Date: May 12, 2005

(65) Prior Publication Data
US 2007/0207135 A1  Sep. 6, 2007

(30) Foreign Application Priority Data

Oct. 24, 2003  (AU) ................................. 2003905882

(51) Int. Cl.
| | | |
|---|---|---|
| A01N 59/14 | (2006.01) | |
| A01N 59/00 | (2006.01) | |
| C02F 3/00 | (2006.01) | |
| C02F 1/00 | (2006.01) | |
| C02F 1/68 | (2006.01) | |
| C11D 9/16 | (2006.01) | |

(52) U.S. Cl.
USPC ........... 424/658; 424/600; 424/657; 424/659; 424/660; 210/606; 210/632; 210/764; 510/108; 510/109; 510/461; 510/465; 510/486

(58) Field of Classification Search
None
See application file for complete search history.

(56) References Cited

U.S. PATENT DOCUMENTS

| | | | |
|---|---|---|---|
| 4,684,469 A | 8/1987 | Pedersen et al. | |
| 5,324,432 A | 6/1994 | Robertson et al. | |
| 5,395,530 A | 3/1995 | Robertson et al. | |
| 7,347,941 B2 * | 3/2008 | Sava | 210/606 |
| 2003/0047510 A1 | 3/2003 | Baldridge et al. | |

FOREIGN PATENT DOCUMENTS

| | | |
|---|---|---|
| EP | 0590746 A1 | 4/1994 |
| EP | 0 619 367 A1 | 10/1994 |
| EP | 0871596 A1 | 10/1998 |
| EP | 1113112 A1 | 7/2001 |
| JP | 59-225103 A | 12/1984 |
| JP | 06-262165 A | 9/1994 |
| JP | 08-508770 T | 9/1996 |
| JP | 11-505565 T | 5/1999 |
| JP | 2000-144840 A | 5/2000 |
| JP | 2003-119862 A | 4/2003 |
| JP | 2005-531397 T | 10/2005 |
| WO | WO-92/13807 | 8/1992 |
| WO | WO-9423006 | 6/1994 |
| WO | WO-96/21499 A1 | 7/1996 |
| WO | 9947631 A1 | 9/1999 |
| WO | 2004002896 A1 | 1/2004 |
| WO | WO-2004002896 A1 | 1/2004 |

OTHER PUBLICATIONS

Smith, KM, Bu, Y, Suga, H "Drug Fights Bacteria by Disrupting Quorum Sensing and Biofilms" ScienceBlog.com, Jan. 24, 2003, 2 pages.*
Organic Chemistry Portal "Sodium Perborate" Org. Chem. Portal, Feb. 8, 2007, 2 pages.*
European Search Report dated Oct. 26, 2010, (EP 04761450 ), 3 pages.
Office Action dated Jul. 27, 2010, for corresponding Japanese Patent Application No. P2006-535910, 3 pages.

* cited by examiner

*Primary Examiner* — Jon P Weber
*Assistant Examiner* — Aaron J Kosar
(74) *Attorney, Agent, or Firm* — Edwards Wildman Palmer LLP; Jeffrey D. Hsi

(57) ABSTRACT

A tablet for use in a drip tray including an excipient selected so that the tablet will not fully dissolve in water at ambient temperature for a period of at least one month, more preferably up to 12 months, a biocide, at least one enzyme, preferably a proteolytic or hydrolase enzyme, and enzyme preserving means, such as a boron compound for maintaining enzyme activity in a moist environment. The excipient may be for example poly vinyl alcohols, high molecular weight polyethylene glycols, high molecular weight polypropylene glycols, esters or partial esters of polyethylene glycols or of polypropylene glycols, and high molecular weight thermoplastic surfactants. The invention also relates to methods for inhibiting the growth of biofilm in an drip tray or the like, including the step of adding to the tray a tablet according to the invention.

26 Claims, No Drawings

DRIP TRAY TABLET

FIELD OF THE INVENTION

This invention relates to a tablet for use in preventing biofilm growth in a drip tray and drainage tube from said drip tray and to a method of manufacture thereof. The invention extends to include use of the tablet for prevention of biofilm growth, for example in a drip tray.

BACKGROUND OF THE INVENTION

Drip trays are widely used in industrial and domestic environments where water condenses. For example, in air conditioning systems and the like, it is usual to provide a drip tray under condensation or refrigeration coils. Condensate falling from the coils is collected in a drip tray which is provided with a drain connected to a water waste system or recirculation system. Other situations in which a drip tray is used are commonplace.

A problem with drip trays is that biofilm grows on wet surfaces in the tray. Excessive biofilm growth can result in the drain becoming blocked which in turn can cause the tray to overflow, and cause flooding.

It has been proposed to treat the water or tray surfaces with biocides to inhibit such growth but such systems have been excessively costly in use. The biocides have been non-oxidizing, and have been provided in tablet form. Since non-oxidising biocides are not wide spectrum, i.e. are not effective against certain genera or strains of biofilm-forming organisms, the efficacy of the biocides is reduced over a period of time. Also the microorganisms present in the environment of the non-oxidising biocide over an extended period give rise to increasing resistance of the microorganism to the biocide. Prior art treatments require the tray to be thoroughly cleaned before use and to date no satisfactory answer to the problem in terms of efficacy, biofilm remediation and bacterial resistance has been found. A further difficulty in many cases relates to the trays not being removable and thus being unable to be cleaned since the clearance between the bottom of the coils and the drip tray is normally too limited to allow clear access.

In commercial air conditioning systems, drip trays are usually located in an air treatment plant of the building—an area with restricted access. Often the trays are positioned at a height of up to 5 m, requiring use of a ladder, and their servicing is done by highly qualified technicians, i.e. expensive and time-consuming. It is not uncommon to find a tray that is serviced once every 12-24 months, if at all.

Any discussion of the prior art throughout the specification should in no way be considered as an admission that such prior art is widely known or forms part of common general knowledge in the field.

It is an object of preferred embodiments of the present invention to provide an improved method for controlling biofilm in a drip tray and its drainage line or the like, and to provide a tablet for use in the method, and a method of manufacture of such tablets.

BRIEF STATEMENT OF THE INVENTION

The present inventors have conceived the idea of incorporating an enzyme in a drip tray tablet containing a biocide. This has been found not merely to kill microorganisms, but also to remove biofilm and prevent biofilm drain blockage.

According to a first aspect the invention provides a tablet for use in a drip tray including a slowly soluble excipient, a biocide, at least one enzyme, and enzyme preserving means for maintaining enzyme activity in a moist environment.

By "slowly soluble" is meant an excipient such that the tablet will not fully dissolve in water at ambient temperature for a period of at least one month and preferably will not fully dissolve for a period of more than 6 months or even more preferably will not fully dissolve for a period of more than 12 months. In other preferred embodiments, the tablet will not fully dissolve in water at ambient temperature for a period of 1 to 12 months. In alternate embodiments the period is 1 to 6 months or 6 to 12 months. An example of a suitable excipient is Poly Vinyl Alcohols (PVAs). Other excipients may be selected from high molecular weight polyethyleneglycols, high molecular weight polypropyleneglycols, esters or partial esters of said polyethyleneglycols or polypropyleneglycols, high molecular weight thermoplastic surfactants such as polyoxyethylenecondensates, polyoxypropelene condensates or polyoxyethylenepolyoxypropylene copolymers with appropriate hydrophobes or blends of these and/or other appropriate compounds.

The enzyme may be a single enzyme or a combination of enzymes and preferably is selected from proteolytic and/or hydrolase enzymes.

Incorporating an enzyme into a drip tray tablet is problematic in practice because in use the tablet in the drip tray becomes saturated with water. This destroys the enzyme activity in the non-dissolved part of the tablet in days or weeks, thus reducing the biofilm destroying properties of the enzymes.

According to a second aspect the invention provides a tablet for use in a drip tray including a slowly soluble excipient, a biocide, at least one enzyme, and enzyme preserving means for maintaining enzyme activity in a moist environment wherein the means for preserving the enzyme activity is inclusion in the tablet composition of a boron compound in a concentration sufficient to maintain some enzyme activity for at least three months during use.

A preferred boron compound is borax, which the present inventors have found acts to preserve the enzyme activity in use for at least 3 months in the non-dissolved part of the tablet. The present invention thus provides matching between the enzyme activity and tablet dissolution parameters.

The invention may preferably contain excipient in an amount of from 2 to 95%, more preferably from 10 to 80%, even more preferably from 20 to 60% by weight of the tablet. The biocide may be preferably be present in an amount of from 0.1 to 20%, more preferably 0.5 to 10%, and most preferably from 1 to 5% by weight of the tablet. The enzyme may preferably be present in an amount of up to 10%, more preferably up to 5% and most preferably up to 3% by weight of the tablet. The inhibitor is preferably present in an amount of from 0.1 to 10%, more preferably 0.2 to 5% and most preferably 1 to 3% by weight of the tablet. The enzyme preserving means is present in an amount of from 0.1 to 10% by weight of the tablet, preferably in an amount of from 0.1% to 3% by weight of the tablet.

According to a third aspect the invention provides a tablet for use in a drip tray including a slowly soluble excipient, a biocide, at least one enzyme, enzyme preserving means for maintaining enzyme activity in a moist environment and a surfactant.

According to a fourth aspect the invention provides a tablet for use in a drip tray including a slowly soluble excipient, a biocide, at least one enzyme, enzyme preserving means for maintaining enzyme activity in a moist environment wherein the means for preserving the enzyme activity is inclusion in the tablet composition of a boron compound in a concentration sufficient to maintain some enzyme activity for at least three months during use and a surfactant.

For preference tablets according to the invention are made in a tablet press. Alternatively, the tablets may be made by extrusion and cutting, by pouring into moulds, or by providing in a slow release encapsulation.

For example, a suitable pressure is applied at ambient temperature to a suitable powdered mixture to prepare a tablet according to the invention. The mixture is pressed into a tablet mould (pretreated with a releasing agent if required) to obtain the tablet.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

PREFERRED EMBODIMENTS OF THE INVENTION

A preferred embodiment of the invention will now be described by way of example only.

Example 1

A tablet according to the invention is formulated as follows;

| Chemical Name | Commercial Name | Cas No | Supplier | % w/w |
|---|---|---|---|---|
| C16-C18 Fatty Alcohol Polyethylene Glycol Ether (50EO) | LUHTENSOL AT50 | 102-60-3 | Langdons | 33 |
| Polyvinyl alcohol | GOHSENOL | G105 | Nippon Gohsei | 40 |
| Sodium sulfate | | 7757-82-6 | APS Chem. | 20 |
| Calcium stearate | | | APS Chem | 3 |
| 2 Bromo-2-nitropropane-1,3-diol | BRONOPOL/CAMPRES BNPD | | Canpoint | 2 |
| Subtilsn-Protease Enzyme | SAVINASE 0.9T | 52-51-7 | Novozymes | 2 |
| Borax | | | Spectrum | 1.5 |

The inclusion of a C16-C18 fatty alcohol or other surfactant is optional and depending on water quality may vary from 0.5 to 50% w/w. Different levels of saponification hydrolysis of Poly Vinyl Alcohol may be employed depending on the desired tablet solubility in cold or hot water. For the lowest solubility tablets higher degrees of saponification hydrolysis (e.g. a highly saponified polyvinyl alcohol sold under the trademark GOHSENOL N-500) should be used, while lower saponification hydrolysis of Poly Vinyl Alcohol (e.g. a highly saponified polyvinyl alcohol sold under the trademark GOHSENOL G-105) will result in fast solubilising in cold water.

The amount of sodium sulfate may be varied from about 5 to 70% w/w and acts as a densifier. The calcium stearate is an optional solubility modifier and mould release agent. Other biocides may be substituted for the 2 Bromo-2-Nitropropane-1,3 Diol and the concentration may be varied according to the biocide selected and conditions of use. Similarly other enzymes may be substituted for Savinase 0.9T.

Boric acid or other suitable compounds may be substituted for borax and at least 0.2% w/w will generally be needed.

A tablet according to the invention may be manufactured by the following procedure:

Example 2

20-100 atm pressure is applied at ambient temperature to a powdered mixture having a composition according to Example 1. The mixture is pressed into a tablet mould, pretreated with a releasing agent if required.

A suitable (accelerated) test method is as follows:

A tablet to be tested is placed into a 1 L plastic tray filled with water. A thin jet of cold (approx 20° C.) tap water is introduced in the tray to allow full replacement of water every 10 minutes. The rate of dissolution of the tablet is observed and results are reported every 24 hours. Each 24-hr period of the above test corresponds roughly to 45 days under field conditions.

A tablet prepared in accordance with example 2 has a dissolution rate of 94 hours in the above test.

When Gohsenol N500 (low cold water solubility) is used instead of Gohsenol G105, the dissolution rate increases to 227 hours in the above test (equivalent to around 15 months in the field).

The rate of dissolution of the tablet is preferably maintained at between 4 and 10 days in the above test to correspond to 6-15 months in the field. While it is possible to extend the dissolution rate even further, to do so has been found to compromise biocidal and biofilm removal performance in some cases. Conditions in the field vary and biocide molecules may undergo some changes at extreme temperatures that may be encountered.

Comparison with Prior Art

A commercially available drip tray tablet which is composed of surfactants and biocide was inserted into a first metal drip tray with a flexible, transparent PVC tubing drain line that both had visible biofilm. The plant was situated in the locked plant room of an upper floor of a commercial building. The tablet was placed adjacent to the drain line. Over the ensuing six weeks the tablet not only did not remove the biofilm but the biofilm continued to develop to the extent that the drainage line from the drip tray became blocked. With the only available drainage from the tray closed off the water overflowed from the tray causing water damage to the floor below.

A second identical drip tray sited immediately adjacent to the first tray into which drained the condensate from an identically sized air conditioning cooling coil was at the same time fitted with a tablet with a composition matching that described in example 1. This tray and drain line also had visible biofilm at the time of tablet addition both adjacent to and in the drain line. When the drip trays were inspected after four weeks this drip tray was found to have no biofilm whatsoever in the immediate vicinity of the tablet and a lessened amount nearby. Most notably the biofilm in the drain line had visibly decrease almost to the point of complete removal.

The rate of dissolution of the tablet is largely dependant upon the temperature and humidity. At times of high temperature and humidity the tablet dissolves significantly faster due to the much greater amount of water dripping onto the tablet and may dissolve within four to eight weeks. At the other extreme, if temperatures and humidity are low, a tablet may not dissolve within twenty five to fifty weeks.

The rate of dissolution of the tablet can be largely controlled by varying the soluble high molecular weight components of the formulation, i.e. by increasing the molecular weight and the proportion of this slow dissolving component the tablet will last longer. Alternatively the size of the tablet can be increased. However the rate of solution must be sufficiently high to ensure the efficacy of the enzyme and biocide combination contained in the tablet.

Formulations and methods of manufacture herein disclosed may be altered to an extent which will be apparent to those skilled in the art from the teaching hereof without departing from the inventive concept herein disclosed.

The claims defining the invention are as follows:

1. A tablet for use in a drip tray, the tablet comprising:
   an excipient selected so that the tablet will not fully dissolve in water at ambient temperature for a period of at least three months;
   at least 500 ppm of a biocide;
   at least one enzyme; and
   a boron-containing compound for maintaining enzyme activity in a moist environment; and wherein the tablet inhibits biofilm growth.

2. A tablet according to claim 1 wherein the excipient is selected such that the tablet will not fully dissolve in water at ambient temperature for a period of at least 6 months.

3. A tablet according to claim 1 wherein the excipient is selected such that the tablet will not fully dissolve in water at ambient temperature for a period of at least 12 months.

4. A tablet according to claim 1 wherein the excipient includes one or more compounds selected from the group consisting of poly vinyl alcohols, polyethylene glycols, polypropylene glycols, esters or partial esters of polyethylene glycols or of polypropylene glycols, and thermoplastic surfactants.

5. A tablet according to claim 4 wherein the thermoplastic surfactant is selected from the group consisting of polyoxyethylene condensates, polyoxypropylene condensates, polyoxyethylenepolyoxypropylene copolymers with hydrophobes, and combinations thereof.

6. A tablet according to claim 1 wherein the at least one enzyme is selected from the group consisting of protease and hydrolase enzymes.

7. A tablet according to claim 1 wherein the boron compound is present in a concentration sufficient to maintain enzyme activity for at least three months during use.

8. A tablet according to claim 1 wherein the excipient comprises 2% to 95% by weight of the tablet.

9. A tablet according to claim 8 wherein the excipient comprises 10% to 80% by weight of the tablet.

10. A tablet according to claim 9 wherein the excipient comprises 20% to 60% by weight of the tablet.

11. A tablet according to claim 1 wherein the at least one enzyme comprises up to 20% by weight of the tablet.

12. A tablet according to claim 11 wherein the at least one enzyme comprises up to 10% by weight of the tablet.

13. A tablet according to claim 12 wherein the at least one enzyme comprises up to 5% by weight of the tablet.

14. A tablet according to claim 13 wherein the at least one enzyme comprises up to 3% by weight of the tablet.

15. A tablet according to claim 1 wherein the boron-containing compound is present in an amount of from 0.1% to 10% by weight of the tablet.

16. A tablet according to claim 15 wherein the boron-containing compound is present in an amount of from 0.1% to 3% by weight of the tablet.

17. A tablet according to claim 1 wherein the biocide is present in an amount of from 0.1% to 20% by weight of the tablet.

18. A tablet according to claim 17 wherein the biocide is present in an amount of from 0.5% to 10% by weight of the tablet.

19. A tablet according to claim 18 wherein the biocide is present in an amount of from 1% to 5% by weight of the tablet.

20. A tablet according to claim 1 further including a surfactant.

21. A tablet according to claim 1 wherein the tablet is made in a tablet press.

22. A tablet according to claim 1 wherein the tablet is made by a process comprising a step made by a process including the step of moulding.

23. A tablet according to claim 1 wherein the tablet is made by a process comprising a step of extruding.

24. A tablet according to claim 1 that is a slow release encapsulated tablet.

25. A tablet according to claim 1 wherein the boron-containing compound is borax.

26. A method for inhibiting the growth of a biofilm in a drip tray, comprising the step of adding a tablet to the drip tray, the tablet comprising:
   an excipient selected so that the tablet will not fully dissolve in water at ambient temperature for a period of at least three months;
   at least 500 ppm of a biocide;
   at least one enzyme; and
   a boron-containing compound for preserving enzyme activity in a moist environment, and
   wherein the tablet inhibits said biofilm growth.

* * * * *